US008173688B2

(12) United States Patent
Damaj

(10) Patent No.: US 8,173,688 B2
(45) Date of Patent: May 8, 2012

(54) THIAZOLE COMPOUNDS, AND COMPOSITIONS AND METHODS USING SAME

(75) Inventor: Bassam Damaj, San Diego, CA (US)

(73) Assignee: Nexmed Holdings, Inc., San Diego, CA (US)

( * ) Notice: Subject to any disclaimer, the term of this patent is extended or adjusted under 35 U.S.C. 154(b) by 543 days.

(21) Appl. No.: 12/138,603

(22) Filed: Jun. 13, 2008

(65) Prior Publication Data

US 2009/0311343 A1 Dec. 17, 2009

(51) Int. Cl.
*A61K 31/426* (2006.01)
(52) U.S. Cl. ..................................... 514/367
(58) Field of Classification Search ............... None
See application file for complete search history.

(56) References Cited

U.S. PATENT DOCUMENTS

| | | | |
|---|---|---|---|
| 3,519,630 A * | 7/1970 | Popoff et al. | 514/367 |
| 5,079,255 A | 1/1992 | Katano et al. | |
| 5,141,946 A | 8/1992 | Katano et al. | |
| 5,200,407 A | 4/1993 | Katano et al. | |
| 5,594,145 A | 1/1997 | Forstinger et al. | |
| 5,919,807 A | 7/1999 | Muller et al. | |
| 5,945,425 A | 8/1999 | Moormann et al. | |
| 6,906,078 B2 | 6/2005 | Moorman et al. | |
| 2007/0203236 A1 | 8/2007 | Smith et al. | |
| 2009/0227633 A1 | 9/2009 | Damaj | |

FOREIGN PATENT DOCUMENTS

| | | | |
|---|---|---|---|
| DE | 2135543 | * | 1/1973 |
| EP | 067685 | | 12/1982 |
| WO | WO-03/106430 | | 12/2003 |
| WO | WO-2005/083107 | | 9/2005 |
| WO | WO-2005110979 | | 11/2005 |
| WO | WO-2007073637 | | 7/2007 |
| WO | WO-2007/103273 | | 9/2007 |

OTHER PUBLICATIONS

Rella et al. J. Chem. Inf. Model., 2006, vol. 46, pp. 708-716.*
Makhija et al. Bioorganic & Medicinal Chemistry, 2004, vol. 12, pp. 2317-2333.*
Noguchi et al. Yakugaku Zasshi, 1968, vol. 88, No. 11, p. 1437-1449 (Abstract attached).*
English Translation of DE 2135543 (Machine Translation from EPO website, accessed Aug. 22, 2011).*
Koci, Jan et al., "Heterocyclic Benzazole Derivatives with Antimycobacterial in Vitro Activity," Biorganic & Medicinal Chemistry Letters 12 (2002) 3275-3278.
Zhang, Lin, et als., "7'-Substituted Benzothiazolothio- and Pyridinothiazolothio-Purines as Potent Heat Shock Protein 90 Inhibitors," J. Med. Chem. 2006, 49. 5352-5362.
CAS Registry File, Jan. 3, 2002, Chemical Library, Ambinter.
CAS Registry File, Nov. 27, 2001, Chemical Library, Interchim.
Ammar, David A., et al., Department of Molecular and Cell Biology, University of California, Berkeley, California, U.S., "The Cytoskeleton as a Modulator of Gastric Secretion," Mechanisms and Consequences of Proton Transport, International Proton Transport Conference, 9th, Leura, Australia, Aug. 19-21, 2001.
Chang, Yue, et al., College of Pharmaceuticals and Biotechnology, Tianjin University, Tianjin, Peop. Rep. China, "Synthesis of Me-3407 as an Anti-Ulcer Drug Candidate," Huaxue Gongye Yu Gongcheng Bianjibu, 2005.
Kao, Kaly C., Department of Molecular and Cell Biology, College of Letters and Sciences, University of California at Berkeley, Berkeley, California, U.S., Berkeley Scientific (2003).
Kretser, T. Yu, et al., Herzen Russian State Pedagogical University, St. Petersburg, Russia "Synthesis and Structure of 1-Nitro-4-Benzothiazolylsulfanyl- and Sulfonyl Dienes," Russian Journal of Organic Chemistry, 2005.
Okabe, Susumu, et al., Department of Applied Pharmacology, Kyoto Pharmaceutical University, Misasagi, Yamashina, Kyoto, Japan, "Pharmacological Control of Gastric Acid Secretion Via the Apical Membrane of Parietal Cells in Dogs," International Proton Transport Conference, 9th, Leura, Australia, Aug. 19-21, 2001.
Postovskii, I. Ya, et al., Hydrolytic Cleavage of Aryl and Alkyl 2-Sulfones. I. Mechanism of the Reaction of Cleavage.
Tanaka, Junko, et al., Pharmacology Department, Meiji Seika Kaisha, Ltd., Yokohama, Japan, "Gastric Antisecretory and Anti-Ulcer Effect of ME3407, a New Benzimidazole Derivative, in Rats," Editio Cantor Verlag, 2004.
Urushidani, Tetsuro, et al., Department Pharmacology Toxicology, Faculty Pharmaceutical Sciences, University of Tokyo, Tokyo, Japan, American Journal of Physiology, American Physiological Society, 1997.

* cited by examiner

*Primary Examiner* — James D Anderson
(74) *Attorney, Agent, or Firm* — Goodwin Procter LLP

(57) ABSTRACT

The present invention provides, in part, compounds and compositions including a thiazole moiety, that may be useful, for example, for treating cancers, for example kidney cancer.

5 Claims, No Drawings

THIAZOLE COMPOUNDS, AND COMPOSITIONS AND METHODS USING SAME

BACKGROUND

Cancer is a significant health problem throughout the world. The most frequently diagnosed cancers include colon cancer, lung cancer, breast cancer, prostate cancer, liver cancer, stomach cancer, esophagus cancer, and kidney cancer. These cancers represent a majority of cancers diagnosed in the U.S. population and account for over 90% of the cancer-related death in the U.S.

For example, in adults, the most common type of kidney cancer is renal cell carcinoma, which begins in the cells that line the small tubes within the kidneys. Children are more likely to develop a kind of kidney cancer called Wilms' tumor. The American Cancer Society estimates that almost 51,000 people in the United States are diagnosed with kidney cancer each year. According to the Mayo Clinic, the incidence of kidney cancer is increasing.

In addition to a clear need for treatments to control or inhibit tumor cell growth, such as kidney cancer growth, there is an additional need for treatments that are capable of increasing the sensitivity of existing anti-tumor treatments to cancer cells, e.g. tumor cells. For example, a variety of chemotherapies are available to oncologists which generally reduce the rate of a tumor progression. Intrinsic or acquired tumor-mediated drug resistance, however, is major clinical obstacle that can result in the lack of tumor responsiveness in patients undergoing treatment.

Because cytotoxic agents remain the mainstay of cancer treatment, and because the oral and gastrointestinal mucosa is often significantly damaged by cancer therapy, management of these agents and associated effects is an important challenge for oncologists, and there remains a need for agents that minimize side effects and/or can be administered with cytotoxic agents to minimize such effects.

SUMMARY

The present invention provides compounds and compositions as disclosed herein. Further, methods of treating cancers, for example kidney cancer, by administering to a patient in need thereof a disclosed compound or composition are disclosed herein.

For example, provided herein is a composition suitable for administering to a patient, comprising:
a) a compound represented by formula I:

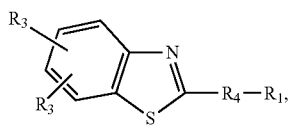

wherein $R_1$ is selected from the group consisting of: -alkylene-$R_5$—$R_6$—$R_2$, —$R_6$—C(O)-phenyl, —$R_6$-phenyl, alkyl, alkenyl or alkynyl, wherein the phenyl, independently for each occurrence, is optionally substituted by one or two moieties selected from the group consisting of halo, alkyl, CN, or $NO_2$;
$R_2$ is a heteroaryl optionally substituted by at one, two or three positions by halo, CN or alkyl;
$R_3$, independently for each occurrence, is selected from the group consisting of H, halo, CN, and $NO_2$;
$R_4$ is selected from the group consisting of thio, sulfonyl, or sulfinyl;
$R_5$ is selected from the group consisting of thio, sulfonyl, or sulfinyl; and
$R_6$ is alkylene or a bond; or pharmaceutically acceptable salts thereof; and
b) a pharmaceutically acceptable excipient.

$R_2$ for example, may be a bicyclic or monocyclic heteroaryl. In certain embodiments, $R_2$ may be selected from the group consisting of benzothiazole, benzooxazole, isoquinoline, and pyridine.

In another embodiment, at least one $R_3$ is $NO_2$ and/or $R_1$ is alkyl or -alkylene-phenyl. For example, $R_1$ may be methylbenzene, optionally substituted at one position by halo or $R_1$ may be ethyl or methyl. In certain embodiments, least one $R_3$ is H. In another embodiment, $R_6$ is a bond. $R_5$, maybe, for example, S. In certain other embodiments, $R_4$ is sulfonyl.

The disclosed compositions may also include a chemotherapeutic agent, for example a chemotherapeutic agent selected from the group consisting of cisplatin, 5-fluorouracil, and vinblastine.

An article of manufacture comprising packaging material and a pharmaceutical composition contained within the packaging material is also provided, wherein the packaging material comprises a label which indicates that the pharmaceutical composition can be used for treatment of cancer and/or gastrointestinal symptoms, alone or in conjunction with administration of chemotherapeutics, and wherein the pharmaceutical composition comprises at least one compound of formula I, as shown and described above.

Also provided herein is a method of treating cancer, e.g. kidney cancer, ovarian cancer, leukemia, lung cancer, bladder cancer, breast cancer, liver cancer, or thyroid cancer, in a patient in need thereof, comprising administering an effective amount of at least one compound represented by formula II:

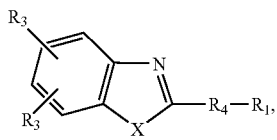

wherein
X is selected from the group of O, NR' and S; wherein R' is H or alkyl;
$R_1$ is selected from the group consisting of: -alkylene-$R_5$—$R_6$—$R_{12}$, —$R_6$—C(O)—$R_{12}$, —$R_6$—$R_{12}$, alkyl, alkenyl, or alkynyl;
$R_4$ is selected from the group consisting of thio, sulfonyl, or sulfinyl;
$R_5$ is selected from the group consisting of thio, sulfonyl, or sulfinyl;
$R_6$ is alkylene or a bond;
$R_{12}$ is an aryl or heteroaryl optionally substituted by at one, two or three positions by halo, hydroxyl, mercapto, nitro, formyl, formamido, carboxy, cyano, amino, amido, carbamoyl, sulphamoyl, ureido, alkyl, alkenyl, alkynyl, alkoxy, alkanoyl, or alkoxycarbonyl, and
$R_3$, independently for each occurrence, is selected from the group consisting of H, halo, cyano, hydroxyl, carboxy, alkyl, alkoxy, and nitro;
or pharmaceutically acceptable salts thereof.

$R_{12}$ of formula II may be for example a heteroaryl optionally substituted by at one, two or three positions by halo, CN or alkyl, e.g. a bicyclic or monocyclic heteroaryl. For example, $R_{12}$ may be, in certain embodiments, selected from the group consisting of benzothiazole, benzooxazole, isoquinoline, and pyridine.

In other embodiments, at least one $R_3$ is $NO_2$ and/or $R_1$ is alkyl or -alkylene-phenyl. $R_1$, in another embodiment, may be is methylbenzene, optionally substituted at one position by halo, or may be ethyl or methyl.

In certain embodiments, least one $R_3$ is H. In another embodiment, $R_6$ is a bond. $R_5$ may be S in certain embodiments and/or $R_4$ may be sulfonyl.

Such methods may further comprise administering another chemotherapeutic agent, such as cisplatin, 5-fluorouracil, or vinblastine. For example, a chemotherapeutic agent and a compound of formula II may be administered together in the same dosage form, or administered together in the separate dosage forms, either simulataneously or at a different time.

In an embodiment, a method of improving therapeutic efficacy of a chemotherapeutic agent is provided, comprising administering to a patient in need thereof a compound represented by formula II, as shown above.

A method of inhibiting tumor growth is also provided, comprising administering to a patient in need thereof a compound represented by formula II.

DETAILED DESCRIPTION

The present disclosure is directed in part towards compounds and compositions that inhibit tumor growth, e.g. growth of tumor cells such as kidney tumor cells, and methods of making and using the same.

A. Terms and Definitions.

Before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

The term "therapeutic agent" is art-recognized and refers to any chemical moiety that is a biologically, physiologically, or pharmacologically active substance that acts locally or systemically in a subject. Examples of therapeutic agents, also referred to as "drugs", are described in well-known literature references such as the Merck Index, the Physicians Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment.

The term "therapeutic effect" is art-recognized and refers to a local or systemic effect in animals, particularly mammals, and more particularly humans caused by a pharmacologically active substance. The term thus means any substance intended for use in the diagnosis, cure, mitigation, treatment or prevention of disease or in the enhancement of desirable physical or mental development and/or conditions in an animal or human. The phrase "therapeutically-effective amount" means that amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of ordinary skill in the art. For example, certain compositions of the present invention may be administered in a sufficient amount to produce a at a reasonable benefit/risk ratio applicable to such treatment.

The term "modulation" is art-recognized and refers to up regulation (i.e., activation or stimulation), down regulation (i.e., inhibition or suppression) of a response, or the two in combination or apart.

A "patient," "subject" or "host" to be treated by the subject method may mean either a human or non-human animal.

The term "treating" is art-recognized and refers to curing as well as ameliorating at least one symptom of any condition or disease.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer, e.g. from 1 to 6 carbons. Likewise, cycloalkyls have from about 3 to about 10 carbon atoms in their ring structure, and alternatively about 5, 6 or 7 carbons in the ring structure. The term "alkyl" is also defined to include halosubstituted alkyls.

Moreover, the term "alkyl" (or "lower alkyl") includes "substituted alkyls", which refers to alkyl moieties having substituents replacing a hydrogen on one or more carbons of the hydrocarbon backbone. Such substituents may include, for example, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CN and the like. Exemplary substituted alkyls are described below. Cycloalkyls may be further substituted with alkyls, alkenyls, alkoxys, alkylthios, aminoalkyls, carbonyl-substituted alkyls, —CN, and the like.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively. The term "alkylene" refers to an organic radical formed from an unsaturated aliphatic hydrocarbon; "alkenylene" denotes an acyclic carbon chain which includes a carbon-to-carbon double bond, both of which can be substituted as for alkyls, as discussed above.

Unless the number of carbons is otherwise specified, "lower alkyl" refers to an alkyl group, as defined above, but having from one to about ten carbons, alternatively from one to about six carbon atoms (i.e. $C_{1-6}$) in its backbone structure. Likewise, "lower alkenyl" and "lower alkynyl" have similar chain lengths.

The term "heteroatom" is art-recognized and refers to an atom of any element other than carbon or hydrogen. Illustrative heteroatoms include boron, nitrogen, oxygen, phosphorus, sulfur and selenium.

The term "aryl" is art-recognized and refers to 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "heteroaryl" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF3, —CN, or the like. The term "laryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF3, —CN, or the like.

The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF3, —CN, or the like.

The term "carbocycle" is art-recognized and refers to an aromatic or non-aromatic ring in which each atom of the ring is carbon.

The term "nitro" is art-recognized and refers to —NO2; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —SO2⁻.

The terms "amine" and "amino" are art-recognized and refer to both unsubstituted and substituted amines, e.g., a moiety that may be represented by the general formulas:

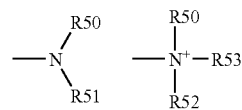

wherein R50, R51 and R52 each independently represent a hydrogen, an alkyl, an alkenyl, —(CH2)m-R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In certain embodiments, only one of R50 or R51 may be a carbonyl, e.g., R50, R51 and the nitrogen together do not form an imide. In other embodiments, R50 and R51 (and optionally R52) each independently represent a hydrogen, an alkyl, an alkenyl, or —(CH2)m-R61. Thus, the term "alkylamine" includes an amine group, as defined above, having a substituted or unsubstituted alkyl attached thereto, i.e., at least one of R50 and R51 is an alkyl group.

The term "amido" is art recognized as an amino-substituted carbonyl and includes a moiety that may be represented by the general formula:

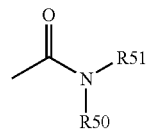

wherein R50 and R51 are as defined above. Certain embodiments of the amide in the present invention will not include imides which may be unstable.

The term "acylamino" is art-recognized and refers to a moiety that may be represented by the general formula:

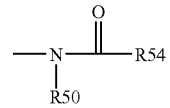

wherein R50 is as defined above, and R54 represents a hydrogen, an alkyl, an alkenyl or —(CH$_2$)m—R61, where m and R61 are as defined above.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—(CH2)m—

R61, wherein m and R61 are defined above. Representative alkylthio groups include methylthio, ethyl thio, and the like.

The term "carbonyl" is art recognized and includes such moieties as may be represented by the general formulas:

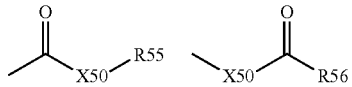

wherein X50 is a bond or represents an oxygen or a sulfur, and R55 and R56 represents a hydrogen, an alkyl, an alkenyl, —(CH$_2$)$_m$—R61 or a pharmaceutically acceptable salt, R56 represents a hydrogen, an alkyl, an alkenyl or —(CH$_2$)$_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The term "amido" is art recognized as an amino-substituted carbonyl and includes a moiety that may be represented by the general formula:

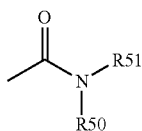

wherein R50 and R51 are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—(CH$_2$)$_m$—R61, wherein m and R61 are defined above. Representative alkylthio groups include methylthio, ethyl thio, and the like.

The term "sulfonyl" is art-recognized and refers to a moiety that may be represented by the general formula:

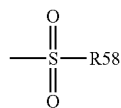

in which, for example, R58 may be one of the following: hydrogen, alkyl, alkenyl, alkynyl, alkylene, cycloalkyl, heterocyclyl, aryl or heteroaryl.

The term "sulfoxido" or "sulfinyl" is art-recognized and refers to a moiety that may be represented by the general formula:

in which R58 is defined above.

The definition of each expression, e.g. alkyl, m, n, and the like, when it occurs more than once in any structure, is intended to be independent of its definition elsewhere in the same structure.

Certain compounds contained in compositions of the present invention may exist in particular geometric or stereoisomeric forms. In addition, polymers of the present invention may also be optically active. The present invention contemplates all such compounds, including cis- and trans-isomers, R— and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, *Handbook of Chemistry and Physics*, 67$^{th}$ Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and non-aromatic organic compounds that may be substituted or unsubstituted.

The term "pharmaceutically-acceptable salts" is art-recognized and refers to the relatively non-toxic, inorganic and organic acid addition salts of compounds, including, for example, those contained in compositions of the present invention. The compounds of this disclosure may be formulated into therapeutic compositions as natural or salt forms. Pharmaceutically acceptable non-toxic salts include the base addition salts (formed with free carboxyl or other anionic groups) which may be derived from inorganic bases such as, for example, sodium, potassium, ammonium, calcium, or ferric hydroxides, and such organic bases as isopropylamine, trimethylamine, 2-ethylamino-ethanol, histidine, procaine, and the like. Such salts may also be formed as acid addition salts with any free cationic groups and will generally be formed with inorganic acids such as, for example, hydrochloric, sulfuric, or phosphoric acids, or organic acids such as acetic, citric, p-toluenesulfonic, methanesulfonic acid, oxalic, tartaric, mandelic, and the like. Salts contemplated herein include amine salts formed by the protonation of an amino group with inorganic acids such as hydrochloric acid, hydrobromic acid, hydroiodic acid, sulfuric acid, phosphoric acid, and the like. Salts may also include amine salts formed by the protonation of an amino group with suitable organic acids, such as p-toluenesulfonic acid, acetic acid, and the like.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof from one organ, or portion of the body, to another organ, or portion of the body. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

B. Compounds and Compositions

In part, this disclosure provides for individuals diastereomers of compounds having the structure (I):

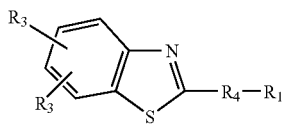

I wherein $R_1$ is selected from the group consisting of: -alkylene-$R_5$—$R_6$—$R_2$, —$R_6$—C(O)-phenyl, —$R_6$-phenyl, alkyl, alkenyl or alkynyl, wherein the phenyl, independently for each occurrence, is optionally substituted by one or two moieties selected from the group consisting of halo, alkyl, CN, or $NO_2$;

$R_2$ is a heteroaryl optionally substituted by at one, two or three positions by halo, CN or alkyl;

$R_3$, independently for each occurrence, is selected from the group consisting of H, halo, CN, and $NO_2$;

$R_4$ is selected from the group consisting of thio, sulfonyl, or sulfinyl;

$R_5$ is selected from the group consisting of thio, sulfonyl, or sulfinyl; and $R_6$ is alkylene or a bond;

or pharmaceutically acceptable salts thereof.

In some embodiments, as described above, any alkylene moiety may be a substituted alkylene moiety. In other embodiments, $R_2$ may be a bicyclic or monocyclic heteroaryl, e.g., benzothiazole, benzooxazole, quinoline, isoquinoline, or pyridine.

One $R_3$ may be, in some embodiments, $NO_2$, and one $R_3$ may be H. In another embodiment, $R_4$ is sulfonyl, e.g. —$S(O)_2$—.

In an embodiment, $R_1$ may be alkylene-S-heteroaryl, e.g. —$CH_2$—$CH_2$—S-heteraryl, where the heteroaryl may be optionally substituted at one, two or three positions by halo, alkyl, CN, or $NO_2$; for example, such heteroaryl may be substituted at only one position by cyano. In another embodiment, $R_1$ may be -alkylene-C(O)-phenyl, e.g. —$CH_2$—C(O)-phenyl, or $R_1$ may be -alkylene-phenyl, e.g. —$CH_2$-phenyl. Such a phenyl moiety, independently for each occurrence, may be optionally substituted by one or two moieties selected from the group consisting of halo, alkyl, CN, or $NO_2$, e.g. substituted by both a CN and $NO_2$. In yet another embodiment, $R_1$ may be chosen from alkyl, alkenyl or alkynyl.

In an embodiment, $R_6$ is a bond.

Also provided are compounds represented by formula II:

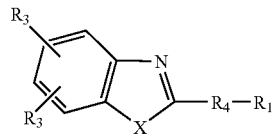

II wherein

X is selected from the group of O, NR' and S; wherein R' is H or alkyl; for example, X may be S;

$R_1$ is selected from the group consisting of: -alkylene-$R_5$—$R_6$—$R_{12}$, —$R_6$—C(O)—$R_{12}$, —$R_6$—$R_{12}$, alkyl, alkoxy, alkenyl, or alkynyl;

$R_4$ is selected from the group consisting of thio, sulfonyl, or sulfinyl;

$R_5$ is selected from the group consisting of thio, sulfonyl, or sulfinyl;

$R_6$ is alkylene or a bond;

$R_{12}$ is an aryl or heteroaryl optionally substituted by at one, two or three positions by halo, hydroxyl, mercapto, nitro, formyl, formamido, carboxy, cyano, amino, amido, carbamoyl, sulphamoyl, ureido, alkyl, alkenyl, alkynyl, alkoxy, alkanoyl, or alkoxycarbonyl, and $R_3$, independently for each occurrence, is selected from the group consisting of H, halo, cyano, hydroxyl, carboxy, alkyl, alkoxy, and nitro;

or pharmaceutically acceptable salts thereof.

In some embodiments, $R_{12}$ may be a bicyclic or monocyclic heteroaryl, e.g., benzothiazole, benzooxazole, quinoline, isoquinoline, or pyridine.

In an embodiment, $R_1$ may be alkylene-S-heteroaryl, e.g. —$CH_2$—$CH_2$—S-heteroaryl, where the heteroaryl may be optionally substituted as defined for $R_{12}$ above.

Compounds that form part of this disclosure include those represented by:

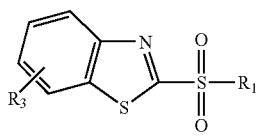

wherein $R_3$ is chosen from H or $NO_2$;
and $R_1$ is chosen from: t-butyl, ethyl, methyl,

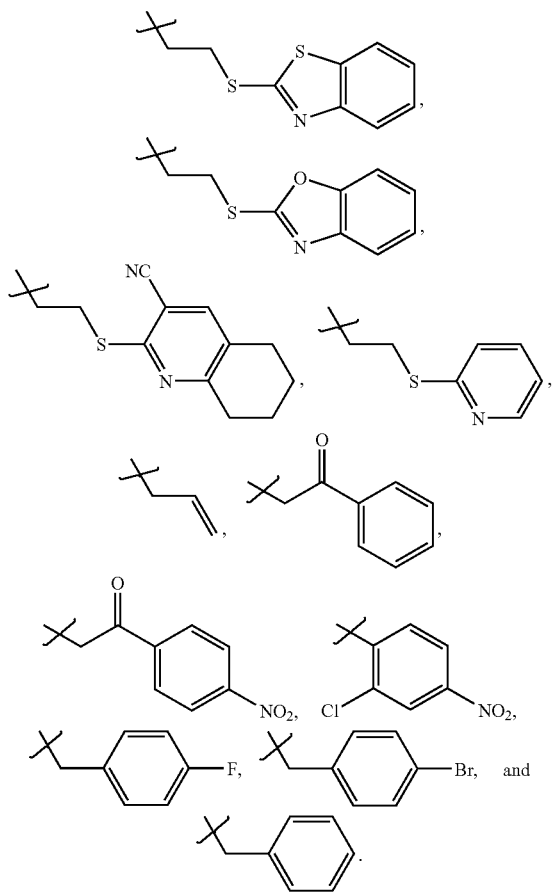

In some embodiments, a composition is provided that includes one or more compounds of formula I or formula II, and a pharmaceutically acceptable excipient.

Compounds of formula I or formula II may, in some embodiments, inhibit $H^+$, $K^+$-ATPase, e.g., have proton pump inhibiting properties.

Compositions disclosed herein may include a buffering agent that, in some embodiments, may protect the compounds against acid degradation. In some embodiments, such buffering agents may include a weak or strong base, and/or may include one or more of sodium bicarbonate, potassium bicarbonate, magnesium hydroxide, magnesium lactate, magnesium glucomate, aluminum hydroxide, aluminum hydroxide/sodium bicarbonate coprecipitate, a mixture of an amino acid and a buffer, a mixture of aluminum glycinate and a buffer, a mixture of an acid salt of an amino acid and a buffer, and a mixture of an alkali salt of an amino acid and a buffer. Additional buffering agents include sodium citrate, sodium tartarate, sodium acetate, sodium carbonate, sodium polyphosphate, potassium polyphosphate, sodium pyrophosphate, potassium pyrophosphate, disodium hydrogenphosphate, dipotassium hydrogenphosphate, trisodium phosphate, tripotassium phosphate, sodium acetate, potassium metaphosphate, magnesium oxide, magnesium hydroxide, magnesium carbonate, magnesium silicate, calcium acetate, calcium glycerophosphate, calcium cholride, calcium hydroxide, calcium lactate, calcium carbonate, calcium bicarbonate, and other calcium salts.

In an embodiment, compositions disclosed herein may also include another chemotherapeutic agent, e.g. anthracyclines (e.g., doxorubicin and mitoxantrone), fluoropyrimidines (e.g., 5-FU, 5-fluorouracil), folic acid antagonists (e.g., methotrexate), podophylotoxins (e.g., etoposide), camptothecins, hydroxyureas, or platinum complexes (e.g., cisplatin). Specific other chemotherapeutic agents include cisplatin, 5-fluorouracil, vinblastin, and irinotecan. Other chemotherapeutic agents may include a taxol, e.g. docetaxel or paclitaxel, etoposide, hormonal antieneoplastics, e.g. leuprolide or tamoxifen, IL-2, vinblastin, and vincristine.

The methods of the present invention contemplate the compositions that include compounds of Formula I administered alone or in combination with other agents (e.g., chemotherapeutic agents or protein therapeutic agents described below).

The compositions of the present invention may contain other therapeutic agents, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques known in the art of pharmaceutical formulation.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration. For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

For topical use, creams, ointments, jellies, solutions or suspensions, etc., containing the compounds of the present invention are employed. In a particular embodiment, compositions contemplated herein may be in the form of eye-drops.

The compounds or compositions disclosed herein can be administered, in some embodiments, with close association with the schedule of another chemotherapeutic. For example, administration can be prior to, simultaneously with or immediately following another therapeutic.

In another embodiment, an article of manufacture comprising packaging material and a pharmaceutical composition contained within the packaging material is provided, wherein the packaging material comprises a label which indicates that the pharmaceutical composition can be used for treatment of cancer and/or gastrointestinal symptoms, alone or in conjunction with administration of chemotherapeutics, and wherein the pharmaceutical composition comprises at least one compound of formula I:

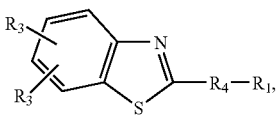

I wherein $R_1$ is selected from the group consisting of: -alkylene-$R_5$—$R_6$—$R_2$, —$R_6$—C(O)-phenyl, —$R_6$-phenyl, alkyl, alkenyl or alkynyl, wherein the phenyl, independently for each occurrence, is optionally substituted by one or two moieties selected from the group consisting of halo, alkyl, CN, or $NO_2$;

$R_2$ is a heteroaryl optionally substituted by at one, two or three positions by halo, CN or alkyl;

$R_3$, independently for each occurrence, is selected from the group consisting of H, halo, CN, and $NO_2$;

$R_4$ is selected from the group consisting of thio, sulfonyl, or sulfinyl;

$R_5$ is selected from the group consisting of thio, sulfonyl, or sulfinyl; and $R_6$ is alkylene or a bond; or pharmaceutically acceptable salts thereof.

C. Methods

Provided herein are methods of treating cancer in a patient in need thereof, comprising administering an effective amount of at least one compound represented by formula II or I, and/or a composition comprising a compound of formula II or I, as described above. Methods of treating cancer contemplated herein include methods of treating kidney cancer, ovarian cancer, leukemia, lung cancer, bladder cancer, breast cancer, liver cancer, thyroid cancer, lymphoma, Hodgkin's lymphoma, melanoma, myeloma, brain cancer, colon cancer, prostate cancer, bone cancer, renal cancer and cervical cancer. Exemplary methods include methods of treating kidney cancer, small-cell lung cancer, non-small cell lung cancer and glioblastoma.

Such methods of treating cancer may also include administering another chemotherapeutic agent, such as those described above. For example, contemplated methods include administering an effective amount of at least one compound represented by formula II or I, and another chemotherapeutic agent in the same dosage form, or in separate dosage forms (either substantially simultaneously or sequentially). Further, when administered in separate dosage forms, one compound or formulation may be administered by one route, whereas the other active ingredient, e.g. another chemotherapeutic, may be administered by a different routes. Alternatively, all the compounds may be administered by the same route.

Also contemplated herein is a method of improving the therapeutic efficacy of a chemotherapeutic agent, comprising administering to a patient in need thereof a compound represented by formula I or II as shown above. For example, the disclosed compounds may have proton pump inhibitory properties, which may lower a tumor cell's resistance to cytotoxic agents. In another embodiment, methods of reducing side effects, e.g. reducing the severity or incidence of side effects associated with the administration of certain chemotherapeutic agents, e.g. methods of reducing the incidence of oral and/or gastrointentinal damage, comprising administering to patient in need thereof (e.g. a patient currently also being administered certain chemotherapeutics) are contemplated Provided herein are methods for inhibiting tumor growth, e.g. reducing the size of a tumor, comprising administering a compound of formula I or II to e.g. reduce the size of tumor. In some embodiments, the survival rate of a patient in need thereof of a compound of formula I or II is greater than about 15% as compard to a subject administered a placebo. Also provided herein are methods for inhibitor tumor cell growth, by administering a compound disclosed herein. Exemplary tumor cells which may be inhibited by such administration include: IGROV1 (ovarian), OVCAR 8 (ovarian), ES-2 (ovarian), CAOV3 (ovarian), OVCAR5 (ovarian), SUDHL4 (lymphoma), RPMI8226 (myeloma), RPMI6666 (Hodgkin's lymphoma), NC37 (lymphoma), GDM-1 (leukemia), MC/CAR (prostate), DU-145 (prostate), J45-01 (leukemia), MOLT3 (leukemia), HUT78, J-gamma-1 (leukemia), MCF7 (leukemia), COLO205 (colon), HL60 CLONE 15 (leukemia), T47D (breast), P116 (intestinal), KU812 (leukemia), SW620 (colon), MK92-M1 (lymphoma), MV-4-11 (leukemia), HS578T (breast), HT29 (colon), HCT 116 (colon), CAKI-1 (kidney), A549 (lung), H460 (lung), A3 (colon), MDA-MB231 (melanoma), MALME 3M (melanoma), RXF393 (kidney), RS4.11 (leukemia), PC3 (prostate), OVCAR3 (ovarian), MDA-MB435 (melanoma), HUT102 (lymphoma), HL60 (leukemia) CCRF-CEM (leukemia), HUT78 (lymphoma), 786-O (kidney), ACHN (kidney), A498 (kidney), H226 (lung), H522 (lung), HO P92 (lung), SNB 19 (brain), OVCAR4 (ovarian), H9 (lymphoma), UO-31 (kidney), HH (lymphoma), DAUDI (leukemia), LOXIMVI (melanoma), NAMALW A (lymphoma), EKVX (lung), DOHH2 (lymphoma), SNB75 (brain), SKMEL28 (melanoma), SKMEL5 (melanoma), SKMEL2 (melanoma), M14 (melanoma), UACC 257 (melanoma), H332M (lung), KM12 (colon), HCC2998 (colon), G401 (kidney), RS1184 (lymphoma), MC116 (leukemia), MOLT4 (leukemia), JMI (liver), HOP-62 (lung), HCT-15 (colon), SF-539 (brain), SF295 (brain), ST486 (lymphoma), U251 (brain), UACC-62 (melanoma).

Preparation of Compounds

Scheme A illustrates a possible method of preparing compounds disclosed herein:

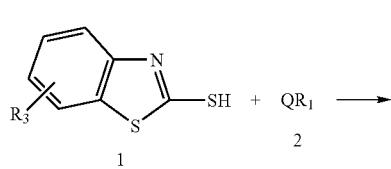

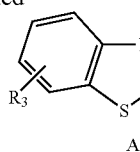

A

Benzothiazole compounds of Formulas I and/or II can be prepared using a 2-thiol compound 1. In an embodiment, 1 reacts with another starting material, 2, wherein Q is a halogen and $R_1$ and $R_3$ are as defined above. The reaction may occur at room temperature in an organic solvent such as ethanol or DMF.

The disclosed compounds may also be prepared by an acid catalyzed reaction of compounds 1 with e.g. 2-amino-benzyl alcohols.

Sulfoxide and sulfonyl containing compounds may be prepared by oxidation of benzothiazoles. Commonly used oxidizing agents include, for example, peracis, such a m-chloroperoxybenzoic acid; perestes; peroxides, such as hydrogen peroxide; sodium mtaperiodiate; selenium dioxide; manganese dioxide, idosobenze; and the like. Such agents can be used in a reaction at a temperature between about 0° C. and about room temperature. Oxidization may be terminated by adding dimethylsulfide. The disclosed compounds can also be prepared with the aid of methods described in U.S. Pat. No. 6,906,078, hereby incorporated by reference.

EXAMPLES

The following examples are provided to further illustrate the advantages and features of the present invention, but are not intended to limit the scope of the invention.

Example 2

Inhibition of a Kidney Tumor Cell Line

Adherent cells are plated approximately 16-24 hours before the day of the experiment in 180 μl growth media. On the day of the experiment, the plated adherent cells are analyzed and counted and suspension cells are plated in 180 μl growth media. The compounds and vehicle are prepared. The resulting solutions are added to the cells. The cells are incubated at 37° C., 5% $CO_2$ for 48 hours. The media is then aspirated. The plate containing the cell suspension is then spun at 1500 RPM for 10 minutes. The media is slowly removed using a multichannel pipettor. 200 μl of MTT is added to each well to a concentration of 0.863 mg/ml MTT in the growth media. The cells are incubated at 37° C., 5% $CO_2$ for 4 hours and then aspirated. The plate containing the cell suspension is then spun at 1500 RPM for 10 minutes. The media is slowly removed using a multichannel pipettor. 100 μl of DMSO is added to each well. The cells are incubated at 37° C., 5% $CO_2$ for 5 minutes and the absorbance is obtained at 560 nm using a Dynex Opsys MR plate reader.

Table 1a and Table 1b indicate the % inhibition of the G401 rhabdoid(kidney) cell line using various compounds as disclosed herein. For several compounds, as noted below, the assay was performed multiple times and the result of each run is reported and associated with a particular compound.

TABLE 1a

| R: | % inhibition G401 (MTT) 20 μM | % inhibition G401 (MTT) 2 μM |
|---|---|---|
| (4-F-phenyl) | 92 | 15 |
| (4-Br-phenyl) | 54 | 15 |
| (phenyl) | 50 | 8 |
| Ethyl | 99 | 10 |
| Methyl | NA | NA |

TABLE 1b

| R: | % inhibition G401 (MTT) 20 μM | % inhibition G401 (MTT) 2 μM |
|---|---|---|
| (benzothiazol-2-ylthio-ethyl) | 91, 64, 102 | 66, 35, 68 |
| (benzoxazol-2-ylthio-ethyl) | 75 | 22 |
| (cyano-tetrahydroquinoline-thio-ethyl) | 63, 63 | 9, 19 |
| (pyridin-2-ylthio-ethyl) | 72 | 9 |
| (allyl) | 72 | 10 |

TABLE 1b-continued

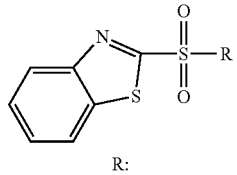

| R: | % inhibition G401 (MTT) 20 μM | % inhibition G401 (MTT) 2 μM |
|---|---|---|
| 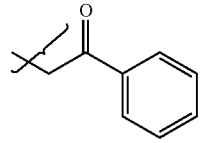 | 78 | 8 |
| 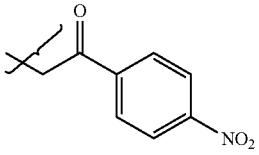 | 100 | 8 |
| 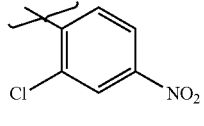 | 95<br>98<br>101 | 9<br>39<br>68 |
| t-Butyl | 26 | 9 |
| Ethyl | NA | NA |
| Methyl | NA | NA |

References

All publications and patents mentioned herein, including those items listed below, are hereby incorporated by reference in their entirety as if each individual publication or patent was specifically and individually incorporated by reference. In case of conflict, the present application, including any definitions herein, will control.

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

The invention claimed is:

1. A pharmaceutical composition comprising:
   a) a compound represented by:

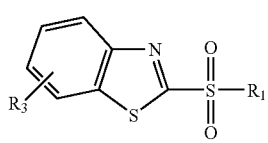

wherein $R_3$ is chosen from H or $NO_2$;

and $R_1$ is chosen from:

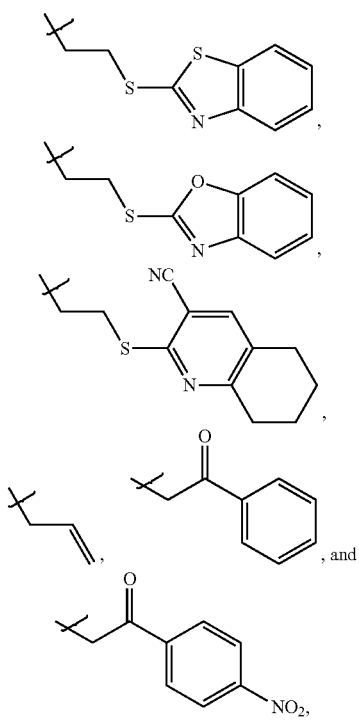

or pharmaceutically acceptable salts thereof; and
   b) a pharmaceutically acceptable excipient.

2. A composition of claim 1, wherein $R^1$ is selected from the group consisting of:

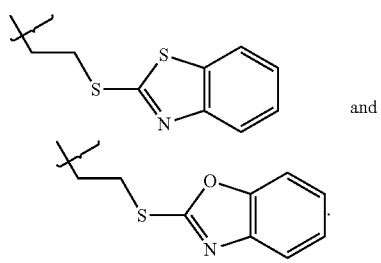

3. A composition of claim 1, wherein $R^1$ is

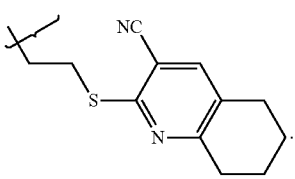

4. A composition of claim 1, wherein $R^1$ is

5. A composition of claim 1, wherein $R^1$ is selected from the group consisting of:
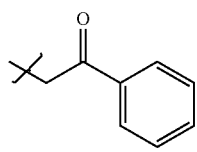
and
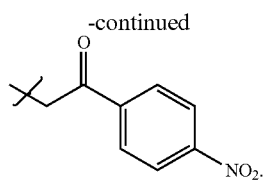
* * * * *